United States Patent
Moen et al.

(10) Patent No.: US 7,799,550 B2
(45) Date of Patent: *Sep. 21, 2010

(54) MICROORGANISM GROWTH SUBSTRATE COMPRISING A BIOMASS DERIVED FROM METHANOTROPHIC BACTERIA

(75) Inventors: Einar Moen, Stavanger (NO); Jeanette Møller Jørgensen, Odense (DK); Karen Møller Jensen, Odense (DK); Arild Johannessen, Stavanger (NO)

(73) Assignee: Statoilhydro ASA, Stavanger (NO)

( * ) Notice: Subject to any disclaimer, the term of this patent is extended or adjusted under 35 U.S.C. 154(b) by 0 days.

This patent is subject to a terminal disclaimer.

(21) Appl. No.: 10/511,685

(22) PCT Filed: Apr. 17, 2003

(86) PCT No.: PCT/GB03/01689

§ 371 (c)(1),
(2), (4) Date: Apr. 22, 2005

(87) PCT Pub. No.: WO03/089625

PCT Pub. Date: Oct. 30, 2003

(65) Prior Publication Data

US 2005/0221465 A1 Oct. 6, 2005

Related U.S. Application Data

(60) Provisional application No. 60/384,815, filed on May 31, 2002.

(30) Foreign Application Priority Data

Apr. 19, 2002 (GB) .................................. 0209007.4

(51) Int. Cl.
*C12N 1/20* (2006.01)
(52) U.S. Cl. .................................................. 435/252.1

(58) Field of Classification Search ...................... None
See application file for complete search history.

(56) References Cited

U.S. PATENT DOCUMENTS 6,689,601 B2 * 2/2004 Koffas et al. ................ 435/247

FOREIGN PATENT DOCUMENTS

| DE | 290 917 | 6/1991 |
| FR | 2311091 | 12/1976 |
| WO | WO 01 60974 | 8/2001 |

OTHER PUBLICATIONS

Patz R et al. Method for the production of biogenic flocculants, DD 290,917 (IDS), English trnaslation, pp. 1-8.*
The term "derive", Merriam-Webster Online Dictionary, at the web: http://www.m-w.com, p. 1.*
Arcangeli J-P & Arvin E, "Modelling the growth of a methanotrophic biofilm: estimation of parameters and variability", Biodegradation, 1999, 10: 177-191; abstract, in particular.*
Atlas RM & Parks LC. "Handbook of microbiological media" 1993 edition, CRC Press, pp. 483-488 and 574-579.*
Atlas RM & Parks LC. "Handbook of microbiological media" 1993 edition, CRC Press, pp. 483-488 and 574-579.*
Bothe et al, *Appl. Microbiol. Biotechnol.*, 59(1):33-39 (2002).
Larsen et al, *Appl. Microbiol. Biotechnol.*, 45:137-140 (1996).
Product Brochure, "BioProtein: A New High Quality Single Cell Protein Based on Natural Gas", issued By Norferm DA, Stavanger, Norway (1998).

* cited by examiner

*Primary Examiner*—Jon P Weber
*Assistant Examiner*—Satyendra K Singh
(74) *Attorney, Agent, or Firm*—Sughrue Mion, PLLC

(57) ABSTRACT

The invention relates to a microorganism growth substrate which comprises a sterile nutrient composition derived from the biomass of a culture of bacteria including methanotrophic bacteria and further containing at least one sterile nutrient. A preferred biomass material is that derived from a microbial culture comprising *Methylococcus capsulatus* (Bath) (strain NCIMB 11132), *Ralstonia* sp. DB3 (strain NCIMB 13287) and *Brevibacillus agri* DB5 (strain NCIMB 13289), optionally in combination with *Aneurinibacillus* sp. DB4 (strain NCIMB 13288).

11 Claims, 3 Drawing Sheets

MICROORGANISM GROWTH SUBSTRATE COMPRISING A BIOMASS DERIVED FROM METHANOTROPHIC BACTERIA

CROSS-REFERENCE TO RELATED APPLICATIONS

This application is a '371 of PCT/GB03/01689, filed Apr. 17, 2003; which claims benefit under 35 U.S.C. §119(e) of U.S. Provisional Application No. 60/384,815, filed May 31, 2002; the disclosure of each of which is incorporated herein by reference.

The present invention relates to the use as a microorganism growth substrate of a bacterial biomass, in particular a biomass, herein termed a "bacterial extract", deriving at least in part from a bacterial culture comprising a methanotrophic bacterium.

Microorganisms are frequently grown on commercial and laboratory scales, for example to produce desired substances from bacterial strains which either naturally produce such substances or have been genetically modified so as to produce such substances, or so as to determine the nature of a bacterial contamination, etc. For these purposes the microorganisms require nutrients and in this regard it is conventional to use yeast, meat or plant extracts which are widely available commercially, e.g. MRS (De Mann, Rogosa and Sharpe), PCA (Plate Count Agar), VRBD (Violet Red Bile Dextrose Agar), YM Agar (Yeast Mould Agar), Baird-Parker Agar Base, VRB Agar (Violet Red Bile Agar), XLD Agar (Xylose Lysine Deoxycholate Agar), CASO (Casein-peptone Soybean-peptone), TSB (Tryptic Soy Broth) and NB (Nutrient Broth). Yeast extract growth substrates (contained for example in MRS, VRBD, VRB Agar, PCA, Baird-Parker Agar Base, and XLD Agar) are available commercially from Merck and Difco among others. Such yeast extracts are commonly produced using biomass from yeast cultures which has been allowed to autolyse, i.e. enzymes naturally occurring within the yeast cells act to break down the cells after cell death. Autolysis of yeast is generally slow and several days may be needed before a suitable degree of digestion is achieved. Accordingly, additives which act as autolysis initiators or stimulators, e.g. thiol agents, are generally used to accelerate the autolysis process. The use of such additives of course adds to the costs of commercial production of yeast autolysates. To the resulting autolysates, extra nutrients may be added to optimize cell growth for particular microorganisms and indeed library deposits of microorganisms will generally specify which growth medium is most suitable for the deposited organism.

Since different microorganisms have different nutritional needs there is of course an ongoing need for alternative and improved microorganism growth media, particularly for growth media effective for growing those microorganisms which are challenging to grow in vitro (e.g. lactobacilli) and for "broad spectrum" growth media which may be suitable for use with unknown microorganisms.

We have now surprisingly found that particularly effective microorganism growth media may be produced using the biomass harvested from a culture medium comprising methanotrophic bacteria, e.g. biomass produced as described in WO 01/60974.

Viewed from one aspect therefore the present invention provides the use of a sterile nutrient composition derived from the biomass of a culture of bacteria including methanotrophic bacteria, and optionally containing further nutrients, as a microorganism growth medium.

The bacterial culture used to produce the biomass is preferably at least 50%, more preferably at least 60%, especially at least 70%, in particular at least 75%, e.g. 75 to 95%, more particularly 75 to 80%, by weight methanotrophic bacteria (relative to the total bacterial weight).

Viewed from a further aspect the invention provides a method of culturing microorganisms which comprises bringing together a microorganism and a growth medium therefor, characterised in that said growth medium is or is prepared from a sterile nutrient composition derived from the biomass of a culture of bacteria including methanotrophic bacteria, optionally with the addition of further nutrients.

Viewed from a yet further aspect the invention provides a microorganism growth substrate comprising a sterile nutrient composition derived from the biomass of a culture of bacteria including methanotrophic bacteria, further containing at least one sterile nutrient, and optionally containing a diluent.

The biomass from which the growth medium or substrate is prepared is preferably biomass generated from at least one species of methanotrophic bacteria and at least one species of heterotrophic bacteria, preferably grown in the same culture medium, e.g. using a loop reactor provided with methane, oxygen, ammonia, and mineral feeds. Suitable combinations of bacteria for generating the biomass are described for example in WO 01/60974 the contents of which are incorporated by reference. One particularly suitable combination is *Methylococcus capsulatus* (Bath) (strain NCIMB 41526), *Ralstonia* sp. DB3 (strain NCIMB 41527), *Aneurinibacillus* sp. DB4 (strain NCIMB 41528) and *Brevibacillus agri* DB5 (strain NCIMB 41525). Each strain was deposited at the National Collection of Industrial and Marine Bacteria Ltd. (NCIMB Ltd.), located at Ferguson Building, Craibstone Estate, Bucksburn, Aberdeen, AB21 9YA, Scotland, UNITED KINGDOM, on Dec. 4, 2007.

The biomass from the bacterial culture may be used directly (although generally after dewatering and sterilization) or it may first be processed to break down the bacterial cells, e.g. by homogenization, hydrolysis or autolysis. Such treatments are described in WO01/60974 and International Patent Application Nos. PCT/GB03/000610 and PCT/GB03/000640 filed 12 Feb. 2003 which are also incorporated herein by reference. (Copies of these two International Patent Applications are also filed herewith.) While homogenizate, hydrolysate and autolysate, especially dried homogenizate and more especially dried autolysate, of the bacterial biomass are the preferred materials for the preparation of microorganism growth media according to the invention, precursor materials obtained by filtration (e.g. ultra filtration) of the homogenized, autolysed or hydrolysed biomass, i.e. the liquid filtrate itself and the retentate, may also be used. Most preferred however is the dried autolysate.

The microorganism growth medium may be the bacterial biomass product itself or a composition containing the biomass product and further constituents, e.g. a liquid or non-liquid carrier or diluent (such as water, gel (e.g. agar gel), or a gellable liquid), and materials such as minerals, carbon sources (such as saccharides (e.g. mono, di, oligo and polysaccharides, especially mono and disaccharides)), nitrogen sources (e.g. nitrates, proteins or protein fragments, ammonium compounds, oligopeptides, amino acids (especially essential amino acids, e.g. tryptophan)), nucleic acids and nucleic acid fragments, lipids, etc. Particularly preferably the medium contains glucose and added nitrate and mineral salts (e.g. potassium, calcium, magnesium, sodium, molybdenum, iron, zinc, boron, cobalt, manganese and nickel compounds), especially glucose. The composition as provided may be a sterile solid (e.g. particulate), a semi-solid or a liquid in ready to use or concentrate form. Especially preferably the composition as provided will be a sterile dry particulate concentrate transformable into a growth medium by the addition of water or an aqueous gelling agent composition.

Wherein the composition contains added glucose, this is preferably in a dry mass basis weight ratio of 5:1 to 1:5 (especially 2:1 to 1:2) relative to the biomass deriving component. Where the composition contains added nitrate and mineral salts this is preferably in a weight ratio of 0.01:1 to 0.2:1 (especially 0.05:1 to 0.1:1) relative to the biomass deriving component. Where the composition as provided contains no added glucose and/or nitrate mineral salts, it is preferred that the preparation of the growth medium involve addition of one or both such components in the weight ratios specified above.

The compositions of the invention are particularly suitable for use as growth substrates for heterotrophic microorganisms, especially heterotrophic algae, yeast or bacteria, in particular anaerobic bacteria such as lactobacilli (e.g. *L. plantarum, L. acidophilus*), aerobic bacteria such as *E. coli*, and algae such as *Crypthecodinium cohnii*.

The invention will now be illustrated further with reference to the following non-limiting Examples and the accompanying Figures in which.

EXAMPLE 1

Biomass Extracts

Figure 1:
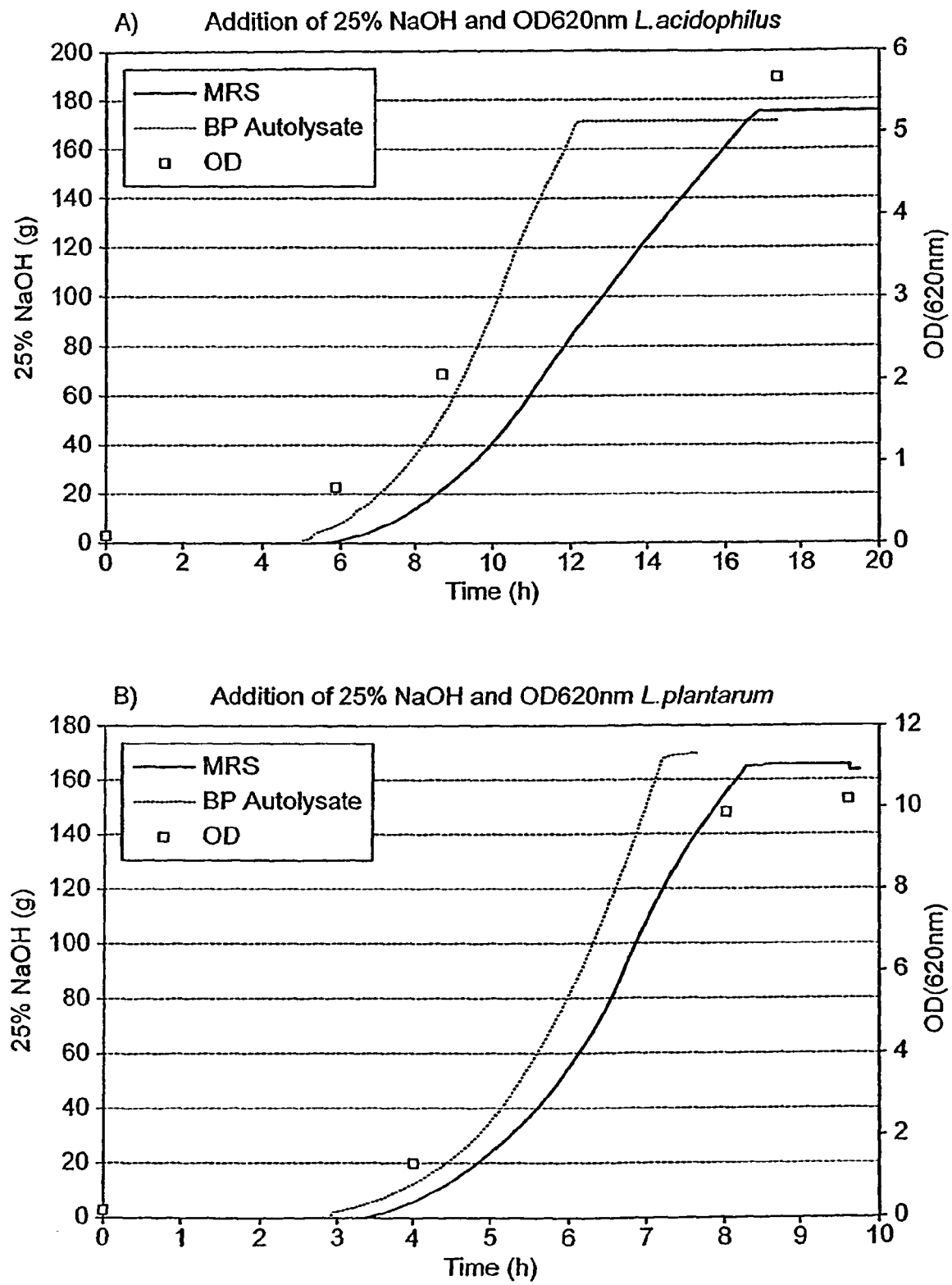
FIG. 1 illustrates results of fermentation studies in a fermentor of A) *L. acidophilus* and B) *L. plantarum* on MRS ( - - - ) and on BP Autolysate ( . . . ). Addition of 25% NaOH (g) and OD 620 nm (for fermentation on MRS) versus time (h).

Methanotrophic and heterotrophic bacteria (*Methylococcus capsulatus* (Bath) (strain NCIMB 41526) *Ralstonia* sp. DB3 (strain NCIMB 41527), *Aneurinibacillus* sp. DB4 (strain NCIMB 41528) and *Brevibacillus agri* DB5 (strain NCIMB 41525), were cultivated as described in WO01/60974 and the resulting biomass harvested and treated as described in WO01/60974 to produce spray-dried homogenizate (hereinafter "BP Homogenizate"), as described in International Patent Application No. PCT/GB03/000610 to produce spray-dried hydrolysate (hereinafter "BP Hydrolysate"), and as described in International Patent Application No. PCT/GB03/000640 (see e.g. Example 1) to produce an autolysate (hereinafter "BP Extract"). Where the post-autolysis ultrafiltration and evaporation steps in the production of "BP Extract" are omitted, the product is referred to herein as "BP Autolysate". Preparation of such a product is described, for example, in Examples 3 and 4 of International Patent Application No. PCT/GB03/000640. The product referred to as "BP Retentate" is an ultra-high-temperature treated biomass that was homogenized. The product referred to as "BP Permeate" corresponds essentially to the product of the ultrafiltration step in the production of "BP Extract".

All materials described above are available from Norferm DA, Norway.

Microorganism growth media were produced by adding BP Homogenizate, BP Autolysate, BP Extract, BP Retentate and BP Permeate to demineralized water at a concentration of 1 g/L. These media were then used either directly or with the addition of 0.1 g/L glucose and/or 32.4 mL/L Nitrate Mineral Salt medium (NMS).

NMS comprises:
1.0 g $KNO_3$
0.2 g $CaCl_2 \cdot 2H_2O$
1.0 g $MgSO_4 \cdot 7H_2O$
0.1 mL trace element solution*
0.1 mL sodium molybdate solution (5 g/L $NaMoO_4 \cdot 2H_2O$ in demineralized water)
0.1 mL EDTA solution (45 g/L $FeNaEDTA \cdot 2H_2O$ in water)
water—to 1 L
10 mL/L sterile phosphate buffer (35.6 g $Na_2HPO_4 \cdot 2H_2O$, 26.0 g $KH_2PO_4$ and water to 1 L) was added.
*6.4 g $ZnSO_4 \cdot 7H_2O$
150 mg $H_3BO_3$
600 mg $CoSO_4 \cdot 7H_2O$
130 mg $MnCl_2$
100 mg $NiCl_2 \cdot 6H_2O$
demineralized water—to 1 L All media were autoclaved before use.

An agar-based microorganism growth medium was also prepared containing:
32.2 g/L BP Extract
20.0 g/L glucose
34 mL/L NMS medium
14.0 g/L agar
demineralized water to 1 L This was autoclaved before use.

EXAMPLE 2

Microorganism Growth Tests

Aerobic and anaerobic, Gram positive and Gram negative bacteria were grown in a shake flask using the liquid growth media of Example 1 and, as controls, growth media recommended for the bacterial strains. The optical density of the cultures was monitored as an indicator of the obtained bacterial growth (i.e. the "plateau" or stationary phase with the highest number of cells). The results are set out in Table 1 below.

TABLE 1

| Bacterium | *Pseudomonas aeruginosa* | *Bacillus subtilis* | *Lactobacillus plantarum* | *Escherichia coli* |
|---|---|---|---|---|
| Characteristics | G(−), aerob | G(+), aerob | G(+), anaerob | G(−), aerob |
| Control Substrate | CASO | NB | MRS | TSB |
| BP Homogenisate | + | +++ | +++ | + |
| BP Extract | +++ | +++ | +++ | +++ |
| BP Autolysate | --- | +++ | +++ | +++ |
| BP Retentate | + | +++ | +++ | +++ |
| BP Permeate | + | + | +++ | --- |

---: No combinations of the BP derivative were better than control substrate.
+: Some combinations of the BP derivative were as good as the control substrate.
+++: Some combinations of the BP derivative were clearly better than control substrate.

For *E. coli*, BP Extract with added glucose clearly provided the best growth. For *L. plantarum*, all combinations of BP Extract clearly gave the best growth. For *P. aeruginosa*, all combinations of BP Extract gave the best growth, in particular BP Extract with added glucose. For *B. subtilis*, BP Extract with added glucose and both glucose and NMS added clearly gave the best growth.

EXAMPLE 3

Viability of Unknown Bacteria

Agar gels (PCA, MRS-agar, and BP Extract with agar (Example 1) pH 6.0 and 7.1) were spread with unknown microorganisms taken from a sample of chopped meat. The cultures were incubated for 72 hours at 25° C. and the total plate count was recorded. For BP Extract, log (CFU/g) was between 5 and about 6.6 while for MRS it was less than 1. For PCA log(CFU/g) was about 6.7, i.e. barely higher.

EXAMPLE 4

*Lactobacillus* Viability

The *lactobacillus* strains *L. casei* ssp. *rhamnosus* (strain ATCC 7469), *L. delbruekii* ssp. *lactis* (strain ATCC 7830), *L. fermentum* (strain CCUG 30138), *L. gasseri* (strain ATCC 19992), and *L. plantarum* (strain ATCC 8014) were grown under aerobic conditions on MRS agar and BP Extract agar (Example 1). In all cases the viability, measured as log(CFU/mL), was the same or greater for BP Extract. This was most pronounced for *L. delbruekii*. The same strains were also grown on these media under anaerobic conditions and again viability was the same or better in all cases for BP Extract.

EXAMPLE 5

Production of Polyunsaturated Fatty Acids

*Crypthecodinium cohnii* (Seligo) Javornicky (strain ATCC 30772) was grown on a culture medium comprising 9 g/L glucose, 25 g/L sea salt and 2 g/L of either yeast extract (YE) or BP Extract in demineralized water. After two days of incubation, the cells were harvested and the total fatty acid, cell dry weight (CDW) and 22:6 (docosahexaenoic acid) contents were determined. The results are set out in Table 2 below.

TABLE 2

| Culture Medium | CDW (g/L) | Lipid (%) | Lipid (g/L) | 22:6 (%) | 22:6 (g/L) |
|---|---|---|---|---|---|
| YE | 3.2 | 12.0 | 0.39 | 36.1 | 0.139 |
| BP Extract | 4.2 | 7.9 | 0.33 | 40.9 | 0.135 |

Table 2 shows that the CDW and the percentage of the polyunsaturated fatty acid 22:6 was higher when BP Extract was used.

EXAMPLE 6

Growth of *Lactobacillus* in media containing BP Autolysate

Growth of the lactobacillus strains *L. plantarum* and *L. acidophilus* on a media with complex components replaced with BP Autolysate (Example 1) was compared to that using standard MRS-media in flasks and in fermentations.

Experiments in Flasks:

*Lactobacillus* was grown in anaerobic flasks to compare the properties of BP Autolysate to that of existing products on the market. The complex components in MRS-media (see Table 3) were substituted with BP Autolysate according to Table 4 such that the total Nitrogen content was kept constant.

TABLE 3

Total Nitrogen (%) in the complex media components

|  | Total Nitrogen (%) |
|---|---|
| Bacto peptone (Oxoid) | 14 |
| Beef Extract, desiccated (Difco) | 14 |
| Yeast Extract (Difco) | 10.9 |
| BP Autolysate (Norferm) | 10.5 |

TABLE 4

Complex media components

| Media | Peptone bacteriological (g/l) | Beef Extract (g/l) | Yeast Extract (g/l) | BP Autolysate (g/l) |
|---|---|---|---|---|
| MRS | 10 | 10 | 5 | 0 |
| CA-1 |  | 10 | 5 | 13 |
| CA-2 | 10 |  | 5 | 13 |
| CA-3 | 10 | 10 |  | 5 |
| CA-4 |  |  |  | 32 |

Experiments in Fermenter:

Two fermentations were performed on each strain; one with a standard media, MRS, and one in which the complex components in MRS were replaced by BP Autolysate (media CA-4 in the flask experiment).

Methods for Experiments Performed in Anaerobic Flasks:

Inoculum: 1 ml seed lot of *L. plantarum* and *L. acidophilus* was used to inoculate 80 ml MRS-broth (Oxoid) and incubated at 37° C. for 20 h. For the strain *L. acidophilus* the MRS-broth was adjusted to pH 5.5.

Cultivation conditions: The complex media substrates were used according to Table 4 while the other media components were kept constant (Table 5). All components except glucose were mixed, the pH was adjusted to 6.0 and pH 5.5, respectively and autoclaved at 121° C., 20 min. The glucose was autoclaved separately. The flasks were flushed with nitrogen before inoculation.

Two flasks were inoculated and one was used as control. 0.5 ml inoculum was used per flask. The flasks were inoculated sidewise at 37° C., 100 rpm in 20 h and 24 h respectively. Samples were analysed for pH and CFU/ml.

TABLE 5

Media composition for experiments in anaerobic flasks

| Component | MRS | CA-1 | CA-2 | CA-3 | CA-4 |
|---|---|---|---|---|---|
|  | (g/l) |  |  |  |  |
| Bacto peptone | 10.0 |  | 10.0 | 10.0 |  |
| Beef Extract, desiccated | 10.0 | 10.0 |  | 10.0 |  |

TABLE 5-continued

Media composition for experiments in anaerobic flasks

| Component | MRS | CA-1 | CA-2 | CA-3 | CA-4 |
|---|---|---|---|---|---|
| | | | (g/l) | | |
| Yeast extract | 5.0 | 5.0 | 5.0 | | |
| BioProtein Autolysate | 0.0 | 13.0 | 13.0 | 5.0 | 32.0 |
| $K_2HPO_4$ | 3.0 | 3.0 | 3.0 | 3.0 | 3.0 |
| $KH_2PO_4$ | 3.0 | 3.0 | 3.0 | 3.0 | 3.0 |
| NaAc | 5.0 | 5.0 | 5.0 | 5.0 | 5.0 |
| $(Na)_3$-citrate | 2.4 | 2.4 | 2.4 | 2.4 | 2.4 |
| $MgSO_4*7H_2O$ | 0.20 | 0.20 | 0.20 | 0.20 | 0.20 |
| $MnSO_4*7H_2O$ | 0.05 | 0.05 | 0.05 | 0.05 | 0.05 |
| Tween 80 | 1.0 | 1.0 | 1.0 | 1.0 | 1.0 |
| Glucose | 20.0 | 20.0 | 20.0 | 20.0 | 20.0 |

Methods for Fermentations:

Inoculum: The same conditions were used as for the flask experiments: 1 ml seed lot of *L. plantarum* and *L. acidophilus* was used to inoculate 80 ml MRS-broth (Oxoid) and incubated at 37° C. for 20 h. For the strain *L. acidophilus* the MRS-broth was adjusted to pH 5.5. Cultivation conditions: All fermentation experiments were performed in a 7.5-L Chemap fermentor. Batch runs of 7 L were inoculated with 70 ml inoculum. The complex media substrates were used according to MRS and CA-4 and the rest of the components were kept as in the flask experiment except that $(Na)_3$-citrate (2.40 g/l) was changed to $(NH_4)_3$-citrate (2.00 g/l) (Table 6). All components except glucose were mixed, the pH was adjusted to 6.0 and pH 5.5, respectively and autoclaved at 121° C., 20 min. The glucose was autoclaved separately.

The fermentations were run at 37° C. and the pH was kept constant at pH 5.8 for *L. plantarum* and pH 5.5 for *L. acidophilus* with addition of 25% NaOH. The fermentation was stopped when the addition of NaOH ceased. Precautions were taken to minimize mixing of air into the media. The end product was analysed for CFU on MRS agar (Oxoid) and contamination on blood-agar and TSA (Difco).

TABLE 6

Media composition for fermentations

| Component | MRS | BP Autolysate (CA-4) |
|---|---|---|
| | (g/l) | |
| Bacto peptone | 10.0 | |
| Beef Extract, desiccated | 10.0 | |
| Yeast extract | 5.0 | |
| BP Autolysate | 0.0 | 32.0 |
| $K_2HPO_4$ | 3.0 | 3.0 |
| $KH_2PO_4$ | 3.0 | 3.0 |
| NaAc | 5.0 | 5.0 |
| $(NH4)_3$-citrate | 2.0 | 2.0 |
| $MgSO_4* 7H_2O$ | 0.20 | 0.20 |
| $MnSO_4* 7H_2O$ | 0.05 | 0.05 |
| Tween 80 | 1.0 | 1.0 |
| Glucose | 20.0 | 20.0 |

Results of Experiments in Flasks:

TABLE 7

Flask experiment for production of *L. plantarum*. Composition of the media with respect to the growth substrates (g/L), viability of *L. plantarum* (CFU/mL) and pH after 20 h at 37° C. The other components of the MRS-media were not changed. The pH in the media was adjusted to 6.0. Two parallels were performed for each experiment.

| Medium | Bacto Peptone | Beef Extract | Yeast Extract | BP Autolysate | pH | | Viability [CFU/mL] | |
|---|---|---|---|---|---|---|---|---|
| MRS | 10 | 10 | 5 | 0 | 3.72 | 3.74 | $3.8 \times 10^9$ | $4.4 \times 10^9$ |
| CA-1 | — | 10 | 5 | 13 | 3.71 | 3.74 | $5.5 \times 10^9$ | $4.6 \times 10^9$ |
| CA-2 | 10 | — | 5 | 13 | 3.74 | 3.75 | $4.3 \times 10^9$ | $6.0 \times 10^9$ |
| CA-3 | 10 | 10 | — | 5 | 3.72 | 3.77 | $3.8 \times 10^9$ | $3.8 \times 10^9$ |
| CA-4 | — | — | — | 32 | 3.78 | 3.77 | $7.4 \times 10^9$ | $6.5 \times 10^9$ |

TABLE 8

Flask experiment for production of *L. acidophilus*. Composition of the media with respect to the growth substrates (g/L), viability of *L. acidophilus* (CFU/mL) and pH after 24 h at 37° C. The other components of the MRS-media were not changed. The pH in the media was adjusted to 5.5. Two parallels were performed for each experiment.

| Medium | Bacto Peptone | Beef Extract | Yeast Extract | BP Autolysate | pH | | Viability [CFU/mL] | |
|---|---|---|---|---|---|---|---|---|
| MRS | 10 | 10 | 5 | 0 | 3.99 | 4.02 | $1.2 \times 10^9$ | $1.3 \times 10^9$ |
| CA-1 | — | 10 | 5 | 13 | 3.79 | 3.75 | $1.6 \times 10^9$ | $1.3 \times 10^9$ |
| CA-2 | 10 | — | 5 | 13 | 3.75 | 3.76 | $2.0 \times 10^9$ | $2.1 \times 10^9$ |
| CA-3 | 10 | 10 | — | 5 | 3.95 | 3.98 | $1.2 \times 10^9$ | $1.2 \times 10^9$ |
| CA-4 | — | — | — | 32 | 3.74 | 3.78 | $2.1 \times 10^9$ | $2.4 \times 10^9$ |

Results of Experiments in Fermenters:

For both strains, the CFU and the usage of sodium hydroxide indicates equal or better growth on the media containing BP Autolysate compared to standard complex components in MRS. The fermentation time was for both strains shorter on BP Autolysate than on MRS. The results are summarized in Table 9 and in FIG. 1. No contamination was observed at any time.

TABLE 9

Summary of fermentations on MRS (with complex media components Peptone bacteriological 10 (g/l), Beef Extract 10 (g/l), Yeast Extract 5 (g/l)) and with complex media components exchanged with BP Autolysate 32 (g/l).

|  | L. acidophilus | | L. plantarum | |
| --- | --- | --- | --- | --- |
|  | MRS | BP Autolysate | MRS | BP Autolysate |
| CFU/ml | $1.0 * 10^9$ | $5.7 * 10^9$ | $8.15 * 10^9$ | $1.4 * 10^{10}$ |
| NaOH (g) | 175.0 | 171.5 | 166.0 | 170.5 |
| Fermentation time (h) | 16.8 | 12.2 | 8.5 | 7.5 |

Conclusions:

Both flask and fermentation experiments showed at least equivalent or improved growth on media which include BP Autolysate than standard MRS.

EXAMPLE 7

E. coli Fermentation for β-Galactosidase Production

The aim of the study was to test alternative BP Autolysates as a source of nitrogen in E. coli fermentation. BP Extract and BP Autolysate (Example 1) were tested and compared to a standard yeast extract.

Method:

The oxygen saturation was kept above 20%. The temperature was 37° C. and the pH was 6.8. Initially the fermentation was done in batch mode with 50% C-source and 50% N-source with minerals added. At $OD_{620}$ 10 the remaining N-source was added over a period of one hour. At glucose levels lower than $0.7 gL^{-1}$, glucose was fed. Glucose was also monitored through pH: 1) pH>6.8 glucose feed increased, and 2) pH<6.75 glucose feed reduced and NaOH added.

Feeds:
1. C-source as glucose, and
2. N-source
   a. Yeast Extract
   b. BP Extract
   c. BP Autolysate (at a concentration of 1.5 times that of the Yeast Extract and the BP Extract).

After 4.5 hours ITPG (iso-propyl-beta-D-thiogalactopyranoside) was added as an inducer of β-galactosidase.

Figure 2:
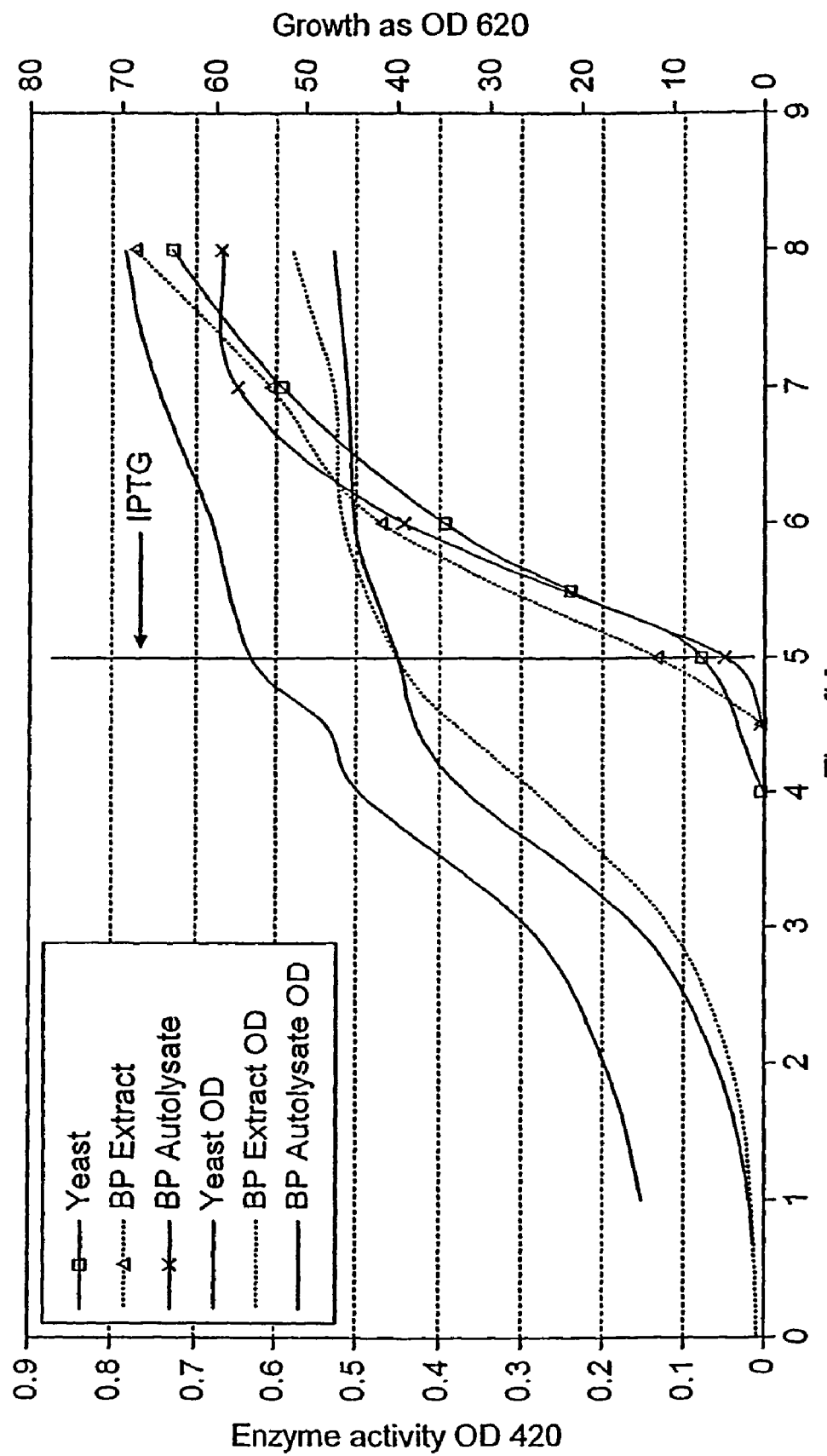
FIG. 2 illustrates data from *E. coli* fermentation studies on yeast extract, BP Extract and BP Autolysate.

Results are shown in FIG. 2 and confirm that the enzyme production was similar for the three N-sources.

EXAMPLE 8

Analysis of BP Autolysate as Complex N-source for L-lysine Overproducing Strains of Corynebacterium Glutamicum NRRL B-11470

The aim of the study was to compare BP Autolysate (Example 1) with soy hydrolysate (Bacto soytone) as a complex N-source for production of lysine by fermentation with a lysine overproducing mutant of C. glutamicum.

Lysine production was compared in fermentations performed in 3 liter glass fermentors with 1 liter medium with C. glutamicum NRRL B-11470. The medium composition was the same in all fermentations except for the complex N-source, which was either BP Autolysate or soytone (14, 21 or 28 g per liter).

Figure 3:
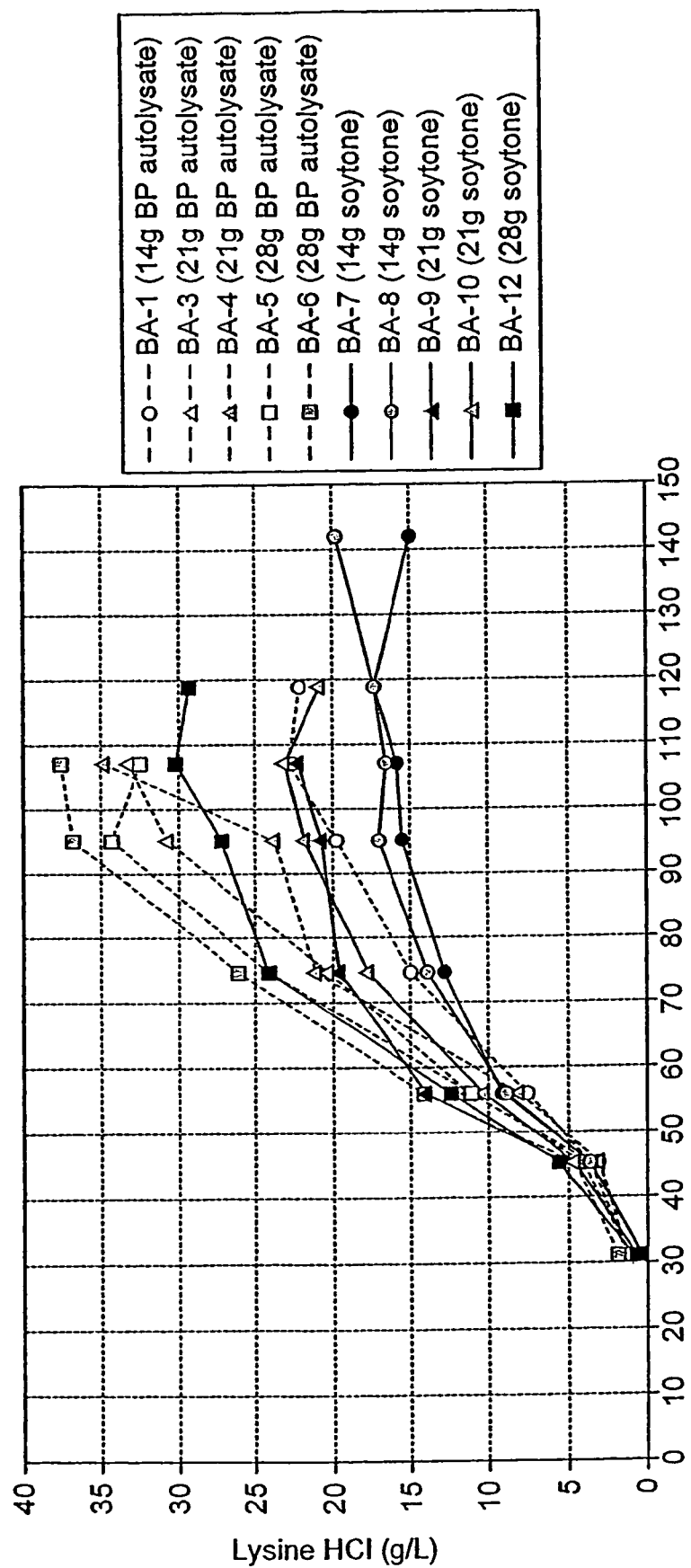
FIG. 3 illustrates lysine production in various fermentations as a function of time and type and amount of added complex N-source.

Results:

The main results of the fermentations are summarized in Table 10. The lysine production as a function of the fermentation time is also shown in FIG. 3.

Generally, the lysine production rate increases with increasing concentration of complex N-source, probably because the cell concentration increases with increasing addition of complex N-source. However, the production rate is significantly higher in cultures to which BP Autolysate is added, than in cultures with the same amount of soytone added. Due to the high concentration of particles in BP Autolysate, it was not possible to determine the optical density in the fermentations with BP Autolysate. Therefore we have no estimate for the cell mass in these fermentations. However, the higher production rate is probably due to a higher cell concentration in the fermentations with BP Autolysate than in the corresponding fermentations with soytone.

TABLE 10

Lysine production with C. glutamicum NRRL B-11470. Summary of the fermentation results.

| Ferm. | Complex N-source Type | Ferm. time g/L | Glucose added (hours) | Final volumetric yield (g) | Volumetric prod. rate (g/L) | Volumetric prod. rate (g/L · hr) | Lysine yield (g lysine HCL/g glucose) between 45-75 hr (g/L · hr) | After 74.4 hours | Final yield[B] | Max. glucose consumption rate (g/L · hr) | Max. carbon expiration rate (CER) (mmol/L · hr) | Accumulated $CO_2$ respiration (mol) | $CO_2$ respiration per unit lysine HCl produced (mmol/g) |
| --- | --- | --- | --- | --- | --- | --- | --- | --- | --- | --- | --- | --- | --- |
| BA-1 | BP Autolysate | 14 | 114.9 | 132 | $23^E$ | 0.20 | 0.40 | 0.17 | 0.18 | 2.4 | 37 | 2.00 | 89 |
| BA-3 |  | 21 | 102.4 | 173 | 33 | 0.32 | 0.57 | 0.17 | 0.21 | 3.4 | 58 | 2.52 | 76 |
| BA-4 |  | 21 | 105.6 | 173 | 35 | 0.33 | 0.62 | 0.18 | 0.22 | 3.4 | 58 | 2.58 | 74 |
| BA-5 |  | 28 | 106.3 | 218 | $35^E$ | 0.33 | 0.70 | 0.16 | 0.18 | 4.7 | 98 | 3.49 | 100 |
| BA-6 |  | 28 | 107.4 | 218 | 37 | 0.35 | 0.74 | 0.18 | 0.19 | 4.5 | 89 | 3.49 | 94 |
| BA-7[C] | Bacto-soytone | 14 | 141.9 | 132 | $18^E$ | 0.12 | 0.31 | 0.15 | 0.14 | 2.1 | 38 | 2.28 | 130 |
| BA-8 |  | 14 | 141.9 | $125^A$ | 20 | 0.14 | 0.35 | 0.15 | 0.17 | 2.1 | 39 | 1.88 | 96 |

TABLE 10-continued

Lysine production with *C. glutamicum* NRRL B-11470. Summary of the fermentation results.

| | | | | | Lysine HCl | | | | | | | $CO_2$ | |
|---|---|---|---|---|---|---|---|---|---|---|---|---|---|
| | | | | | | Volumetric prod. rate | Lysine yield (g lysine HCL/g glucose) | | Max. glucose | Max. carbon | Accumulated | respiration per unit lysine | |
| | Complex N-source | | Ferm. time | Glucose added | Final volumetric yield | Volumetric prod. rate | between 45-75 hr | After 74.4 hours | Final yield[B] | consumption rate | expiration rate (CER) | $CO_2$ respiration | HCl produced |
| Ferm. | Type | g/L | (hours) | (g) | (g/L) | (g/L · hr) | (g/L · hr) | | | (g/L · hr) | (mmol/L · hr) | (mol) | (mmol/g) |
| BA-9 | | 21 | 100.5 | 132 | 22 | 0.22 | 0.51 | 0.18 | 0.18 | 3.3 | 58 | 1.86 | 83 |
| BA-10 | | 21 | 110.4 | 132 | 23[E] | 0.21 | 0.45 | 0.17 | 0.18 | 3.2 | 49 | 1.85 | 80 |
| BA-12 | | 28 | 112.5 | 173 | 30[E] | 0.27 | 0.63 | 0.19 | 0.19 | 4.0 | 63 | 2.55 | 85 |

[A]Glucose consumed. In total 132 g was added, but 7 g/liter was still left when the fermentation was terminated.
[B]The increase in the volume during the fermentation (5-15%) has been taken into account in this calculation.
[C]Despite the fact that microscopic examination of the culture at the termination of the fermentation did not reveal any contaminating organisms in the culture, the analytic results clearly indicate that a contaminating organism was present. However, the organisms do not seem to have affected the lysine production to a large extent
[E]In this fermentation the measured lysine concentration in the last sample is lower than in the last but one sample. This is because the Chinard method has a fairly large standard deviation. The final volumetric yield has been estimated primarily based on the last but one sample.

The final lysine yield per unit glucose was approximately the same in most of the fermentations, 0.17-0.19 g lysine HCl/g glucose, independent of the type and amount of complex N-source added. Possibly, the yield is slightly higher, 0.21-0.22 g lysine HCl/g glucose, in fermentations with 21 g per liter BP Autolysate added.

Conclusions:

The fermentation studies clearly show that BP Autolysate is a good alternative to soytone, and seems to be superior to soytone with respect to production rate in fermentors. The increased production rate is probably due to a higher cell concentration in fermentations with BP Autolysate than in fermentations with the same amount of soytone. The reason for this is unknown, but it may be that BP Autolysate because of its bacterial origin, matches the cell requirements for growth better than soytone with respect to such components as ribonucleic acids, cell wall building components, lipids etc.

The invention claimed is:

1. A sterile microorganism growth substrate comprising:
   (a) a sterilized nutrient composition, wherein said composition is a biomass generated from bacterial cells by autolysis, optionally followed by ultrafiltration and evaporation, wherein said bacterial cells comprise *Methylococcus capsulatus* (Bath) (strain NCIMB 41526), *Ralstonia* sp. DB3 (strain NCIMB 41527), *Aneurinibacillus* sp. DB4 (strain NCIMB 41528) and *Brevibacillus agri* DB5 (strain NCIMB 41525), and wherein said bacterial cells are at least 50% by weight *Methylococcus capsulatus* (Bath) (strain NCIMB 41526) relative to the total bacterial weight;
   (b) sterile glucose; and
   (c) optionally a sterile diluent.

2. The substrate as claimed in claim 1, wherein glucose is present in a weight ratio of 5:1 to 1:5, on a dry mass basis relative to the biomass.

3. The substrate as claimed in claim 2, wherein glucose is present in a weight ratio of 2:1 to 1:2, on a dry mass basis relative to the biomass.

4. The substrate as claimed in claim 1, wherein the sterilized nutrient composition is a dried autolysate of the bacterial biomass.

5. A sterile microorganism growth substrate comprising:
   (a) a sterilized nutrient composition, wherein said composition is a biomass generated from bacterial cells by autolysis followed by ultrafiltration and evaporation, wherein said bacterial cells comprise *Methylococcus capsulatus* (Bath) (strain NCIMB 41526), *Ralstonia* sp. DB3 (strain NCIMB 41527), *Aneurinibacillus* sp. DB4 (strain NCIMB 41528) and *Brevibacillus agri* DB5 (strain NCIMB 41525), and wherein said bacterial cells are at least 50% by weight *Methylococcus capsulatus* (Bath) (strain NCIMB 41526) relative to the total bacterial weight;
   (b) sterile glucose; and
   (c) optionally a sterile diluent.

6. The substrate as claimed in claim 1 or 5, wherein said bacterial cells are grown in a culture medium containing methane, oxygen, ammonia, and mineral feeds.

7. The substrate as claimed in claim 6, wherein said bacterial cells is are 75% to 95% by weight *Methylococcus capsulatus* (Bath) (strain NCIMB 41526) relative to the total bacterial weight.

8. The substrate of claim 1 or 5, wherein nitrate or mineral salts, or combination thereof, are additionally added to the biomass.

9. The substrate as claimed in claim 8, wherein nitrate and mineral salts are present in a weight ratio of 0.01:1 to 0.2:1, relative to the biomass.

10. The substrate as claimed in claim 9, wherein nitrate and mineral salts are present in a weight ratio of 0.05:1 to 0.1:1, relative to the biomass.

11. The substrate as claimed in claim 8, wherein said mineral salts are selected from the group consisting of potassium, calcium, magnesium, sodium, molybdenum, iron, zinc, boron, cobalt, manganese and nickel compounds.

\* \* \* \* \*